(12) United States Patent
Pius

(10) Patent No.: US 7,144,841 B2
(45) Date of Patent: Dec. 5, 2006

(54) FLOWER FOOD DELIVERY MECHANISM WITH EFFERVESCING AGENT

(75) Inventor: Silvester Pius, Summerville, SC (US)

(73) Assignee: Rohm and Haas Company, Philadelphia, PA (US)

( * ) Notice: Subject to any disclaimer, the term of this patent is extended or adjusted under 35 U.S.C. 154(b) by 98 days.

(21) Appl. No.: 10/957,065

(22) Filed: Oct. 1, 2004

(65) Prior Publication Data

US 2006/0073972 A1    Apr. 6, 2006

(51) Int. Cl.
*A01N 3/02*    (2006.01)
(52) U.S. Cl. ..................................... 504/114; 504/115
(58) Field of Classification Search ................ 504/114, 504/115
See application file for complete search history.

(56) References Cited

U.S. PATENT DOCUMENTS

| | | | |
|---|---|---|---|
| 3,874,871 A * | 4/1975 | Sy et al. ..................... 504/115 |
| 5,112,380 A * | 5/1992 | Yamamoto et al. ......... 426/321 |
| 6,083,535 A * | 7/2000 | Chiba et al. ................. 424/489 |
| 6,133,237 A * | 10/2000 | Noll et al. ..................... 514/23 |
| 6,289,630 B1 | 9/2001 | Hetze et al. |
| 6,440,900 B1 | 8/2002 | Koermer et al. |

* cited by examiner

*Primary Examiner*—S. Mark Clardy
(74) *Attorney, Agent, or Firm*—Sonnenschein Nath & Rosenthal LLP

(57) ABSTRACT

Novel cut flower compositions which yield prompt, complete and homogeneous mixing when delivered in a permeable or semi-permeable container. No separate mixing is required, and the resulting solution if free of pH gradients. This result is attained by including in the composition one or more compounds that give rise to gaseous effervescence.

40 Claims, 7 Drawing Sheets

FLOWER FOOD DELIVERY MECHANISM WITH EFFERVESCING AGENT

BACKGROUND OF THE INVENTION

The present invention relates to formulations for maintaining the freshness of flowers and more particularly to kits comprising such formulations in permeable containers.

In order to maximize the fresh appearance of cut flowers, it is known that simply providing water is not sufficient, but rather some type of a cut flower food composition should be provided to the flower. In the past, the standard procedure has been to mix a quantity of powdered cut flower food composition with water to form a solution, with the solution then being provided to the container with the cut flowers. However, this requires the user to properly mix a correct amount of the cut flower food with a correct amount of water in order to achieve a solution with the correct concentration of cut flower food therein. Such a procedure provides mixed results, is time consuming and can be messy.

This problem has been ameliorated with the introduction of cut flower compositions dispensed in metered amounts in permeable containers, or "T-bags." This administration form provides pre-measured quantities of a cut flower food composition packaged in permeable or semi-permeable materials such as a filter paper tea-bag. This assembly can be placed in the water of a container holding cut flowers, after which the water can enter the bag via the filter paper, so that the composition is dissolved, and then carries the composition out of the bag in the dissolved form. Measuring and mixing the proper amount of cut flower composition can therefore be dispensed with.

Unfortunately, however, such compositions in permeable containers suffer from the drawback that the ingredients tend to diffuse from the container in a slow and inhomogeneous fashion, thus yielding a poorly mixed solution. This disadvantage is particularly acute with regard to the pH of the solution. If well mixed, the solution should feature a homogeneous pH of 3 to 4.5, which is the optimal value for preserving the health of the fresh flower foliage. However, presumably due to the poor mixing, it has been observed that a pH gradient is established, and the top of the solution exhibits a pH of 5.5 to 6.5, whereas the bottom, where the cut stem absorbs nutrients and water, features a pH of 2 to 2.4. Such excessively low pH values are harmful to the flower foliage, resulting in a phytotoxic and unpleasant dehydrated appearance.

SUMMARY OF THE INVENTION

It is an object of the present invention to provide a food composition for cut flowers comprising one or more compounds that produce gas when contacted with water.

It is a further object of the present invention to provide a food composition for cut flowers, wherein 100 g of said composition comprise 0.5 g to 10 g of an effervescing agent, and 2.5 g to 60 g of an acid.

Also provided is a kit for maintaining the freshness of cut flowers comprising the food composition for cut flowers, 100 g of said composition comprising 0.5 g to 10 g of an effervescing agent, 2.5 g to 60 g of an acid, and a permeable or semi-permeable container.

Also provided is a solution for maintaining the freshness of flowers comprising for cut flowers, 100 g of said composition comprising 0.5 g to 10 g of an effervescing agent, 2.5 g to 60 g of an acid, and water.

Also provided is an implement for deodorizing air comprising a cut flower and an aqueous solution, wherein the solution comprises a composition, 100 g of said composition comprising 0.5 g to 10 g of an effervescing agent, and 2.5 g to 60 g of an acid.

Another object of the invention is to provide a method for maintaining the freshness of flowers comprising contacting a cut flower with an aqueous solution, wherein said aqueous solution comprises 0.05 g/L to 0.8 g/L of an effervescing agent, and 0.2 g/L to 3 g/L of an acid.

The present invention also provides a cut flower maintained fresh by contacting said cut flower with an aqueous solution, wherein said aqueous solution comprises 0.05 g/L to 0.8 g/L of an effervescing agent, and 0.2 g/L to 3 g/L of an acid.

Also provided is a composition for cut flowers comprising one more compounds selected from the group consisting of compounds comprising one or more azo-moieties, compounds comprising one or more diazo-moieties and chlathrates.

Another object of the invention is to provide an improved food composition for cut flowers, the improvement comprising the composition comprising components that yield gaseous decomposition products.

Furthermore, the present invention provides an improved kit comprising a food composition for cut flowers and a permeable or semi-permeable container, the improvement comprising the composition comprising components that yield gaseous decomposition products.

These and other objects of the invention, as well as the advantages over existing and prior art methods and compositions, which will be apparent in view of the following detailed specification, are accomplished in accordance with the following description and claims.

DETAILED DESCRIPTION OF THE PREFERRED EMBODIMENTS

Figure 1:
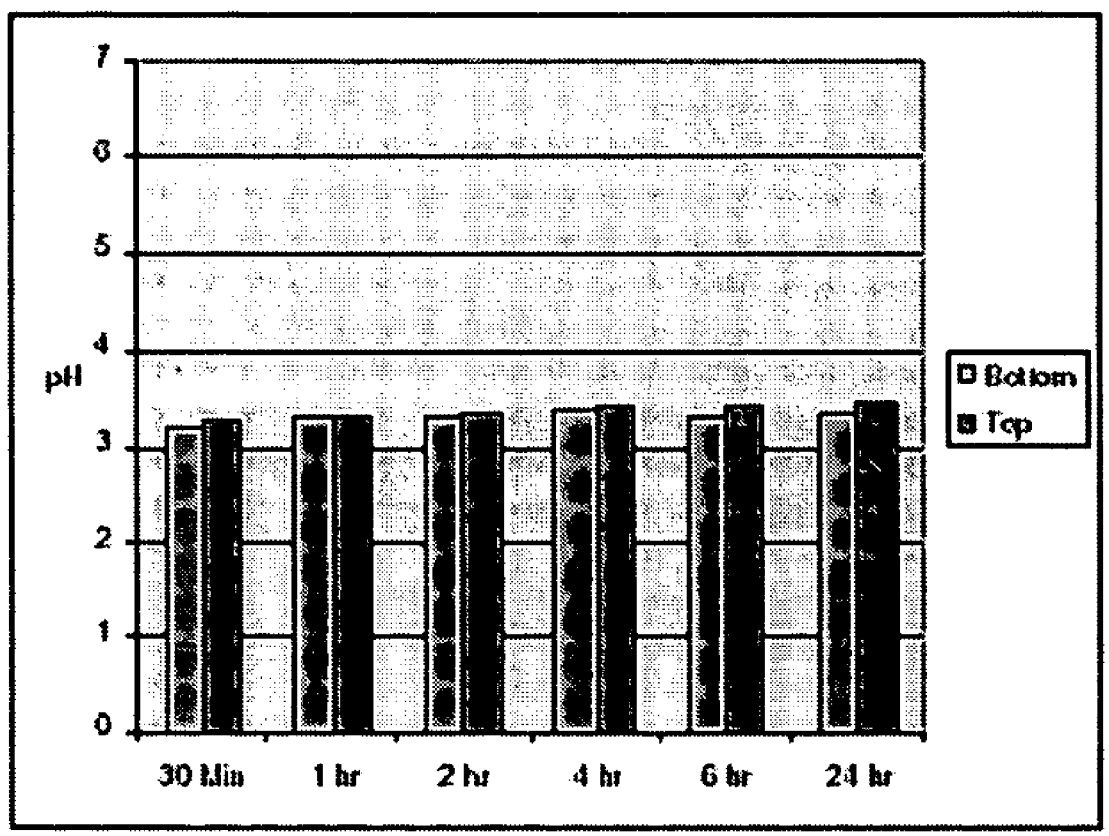
FIG. 1 illustrates the top-bottom pH differential of an unmixed aqueous solution obtained with a EZ DOSE® composition with 4% $CaCO_3$ and citric acid.

The present invention provides novel cut flower food compositions which yield prompt, complete and homogeneous mixing when delivered in a permeable or semi-permeable container. No separate mixing is required, and the resulting solution is free of pH gradients. This result is attained by including in the composition one or more compounds that give rise to gaseous effervescence. One possible explanation for the superior properties of such compositions is that the gas evolving from the effervescence accelerates the dissolution of the components of the mixture from the bag into the water, giving rise to a thoroughly mixed solution in comparatively little time.

In an embodiment of the invention, the effervescence of the composition is obtained by the inclusion in the mixture of components that produce gaseous effervescence upon contact with water. For example, carbonates or bicarbonates which give rise to $CO_2$ gas when protonated, may be used. Example carbonates include $Li_2CO_3$, $Na_2CO_3$, $K_2CO_3$, $(NH_4)_2CO_3$, $MgCO_3$, $CaCO_3$, and example bicarbonates include $LiHCO_3$, $NaHCO_3$ $KHCO_3$ and $NH_4HCO_3$. Other compounds that give rise to gaseous decomposition products when dissolved and/or heated, such as compounds containing azo- or diazo-moieties, chlathrates, peroxides such as $Li_2O_2$, $Na_2O_2$, $K_2O_2$, $MgO_2$ and peroxide-producing compounds such as borax and $NaBO_3$ may also be employed.

In a preferred embodiment of the invention $CaCO_3$ is the compound giving rise to effervescence. The quantity of $CaCO_3$ is preferably 0.5% to 10% of the total weight of the composition, more preferably 2% to 5% of the total weight of the composition, and most preferably 2.8% to 4% of the total weight of the composition.

The effervescence of the composition may be increased by the inclusion of at least one acid to increase the protonation of the carbonates and bicarbonates and their decomposition into $CO_2$. In a preferred embodiment, the acid is an acid, inorganic or organic such as formic, acetic, propionic, butanoic, pentanoic, hexanoic, malonic, tartaric, ascorbic and citric. In a more preferred embodiment, the acid is ascorbic, citric or a mixture thereof. In a yet more preferred embodiment, the acid is citric acid.

The composition also contains carbohydrate compounds customarily present in plant food preparations. Example carbohydrates include dextrose, levulose, fructose, galactose, mannose, sucrose, lactose and maltose. In a preferred embodiment, the carbohydrate is dextrose. The quantity of carbohydrates is preferably 20 g to 95 g for every 100 g of composition, more preferably 60 g to 80 g for every 100 g of composition, and most preferably 65 g to 75 g for every 100 g of composition.

Other plant nutrients may be present in the composition, for example sulfates. Preferred sulfates include $KAlSO_4$ and $MgSO_4$. Various additives may also be included, wherein such additives may be disinfectants, biocides and growth regulators. Example growth regulators include auxins, cytokinins and gibberellins. Conditioning agents for controlling the pH or the hardness of the water may also be part of the composition.

Figure 4:
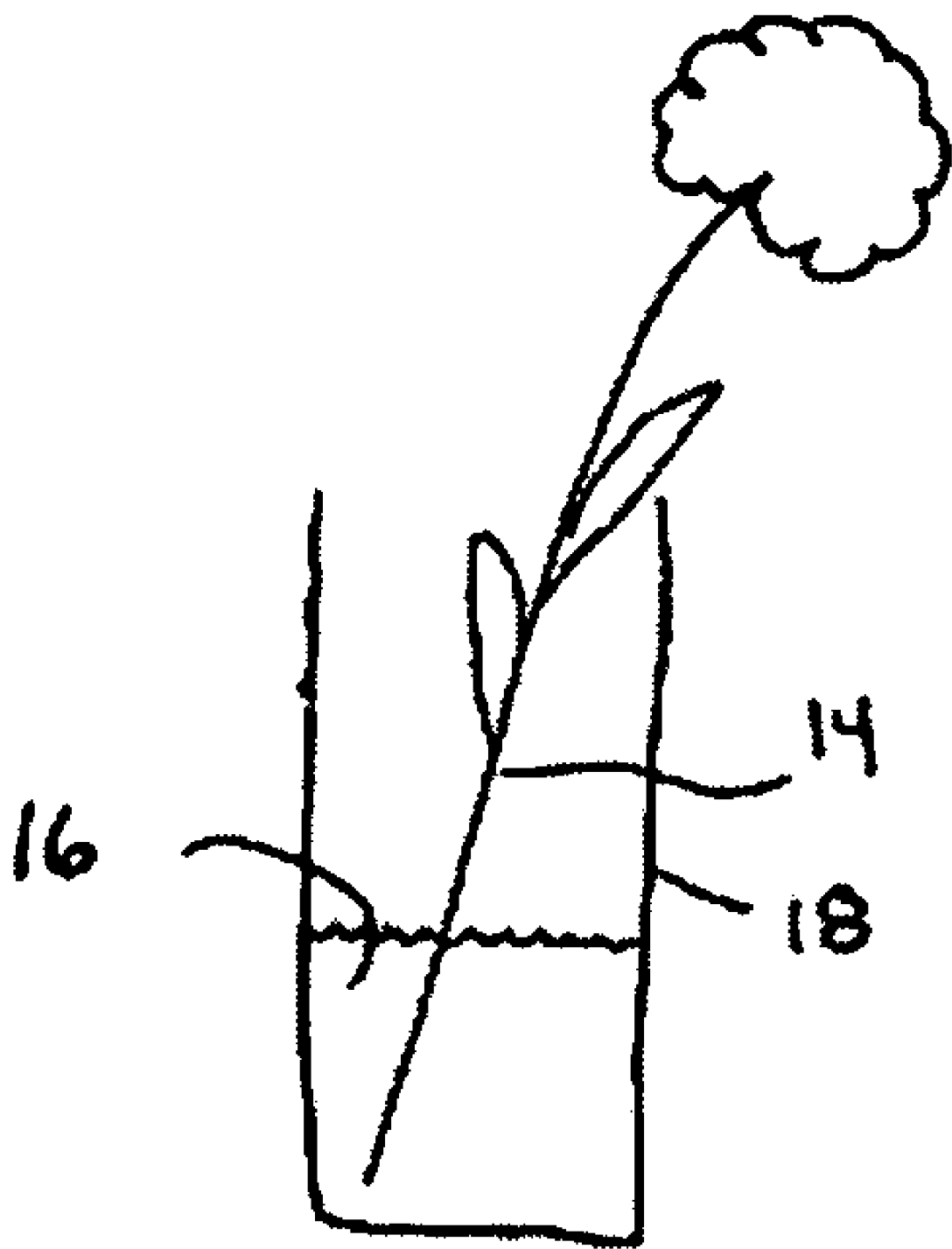
FIG. 4 illustrates a cut flower that has been placed in a novel solution according to the present invention.

FIG. 4 illustrates a cut flower 14 that has been placed in a novel solution 16 held in a container 18 according to the present invention. Such a cut flower 14 with the composition therein comprises an implement for deodorizing air.

Figure 5:
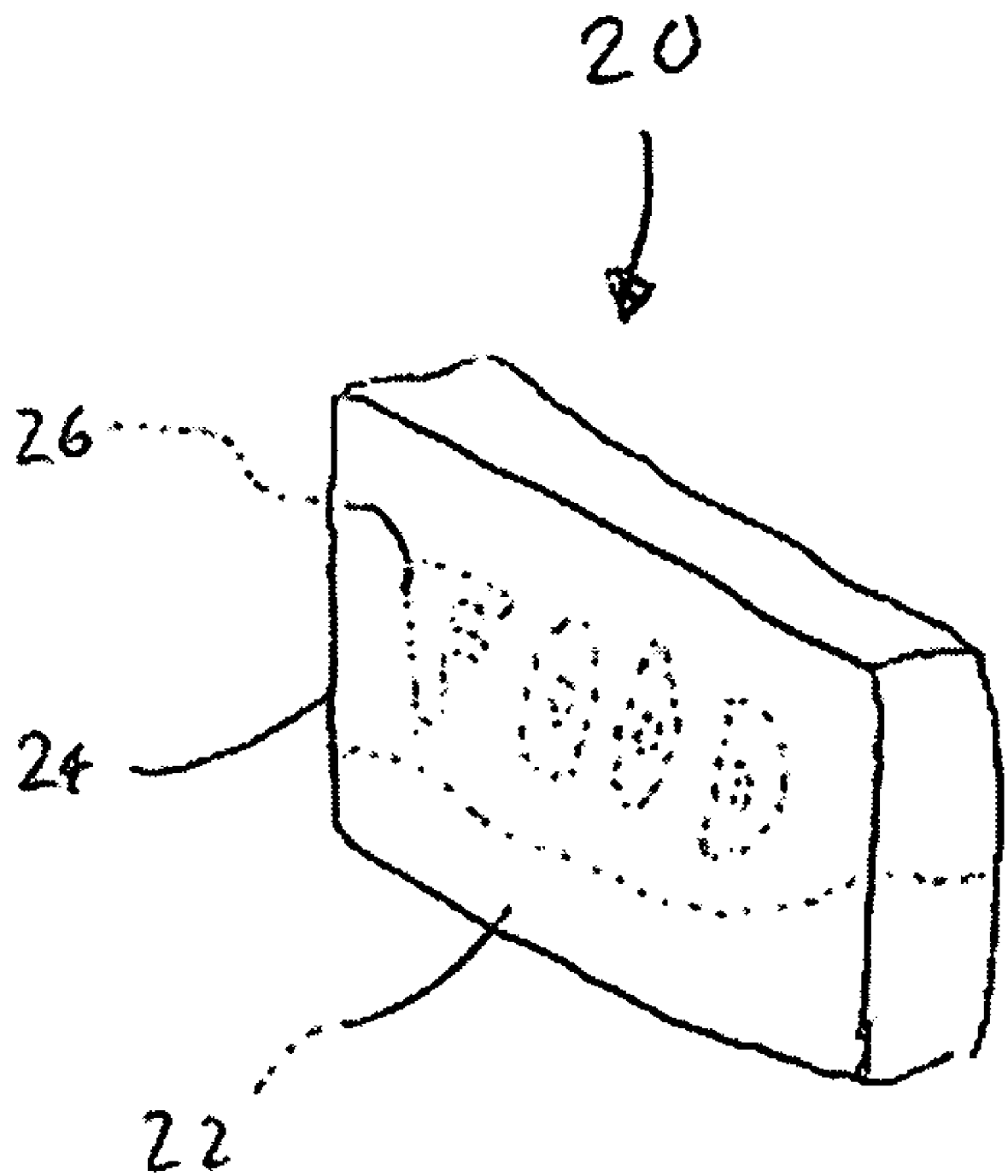
FIG. 5 illustrates a perspective view of a kit comprising a composition and a permeable container.

As shown in FIG. 5, a kit 20 for maintaining the freshness of cut flowers comprises a composition 22 as described above and a container 24. The composition may be provided, for instance, in a powder form or as a solid tablet. The container 24 for delivering the preparation may be made with any water permeable material, for instance filter paper such as that used for manufacturing tea-bags, perforated plastic or cloth, or a metalized material. In a preferred embodiment of the invention, the container 24 is of a semi-permeable material, wherein the term semi-permeable is understood as meaning permeability to particles up to a maximum size of 100 to 400 μm. With a view to ease of production, it is advantageous, in the container 24 according to the invention, if the container is rectangular in shape. In a preferred embodiment, the container is a rectangular bag 2 to 8 cm wide by 2 to 12 cm long.

Figure 6:
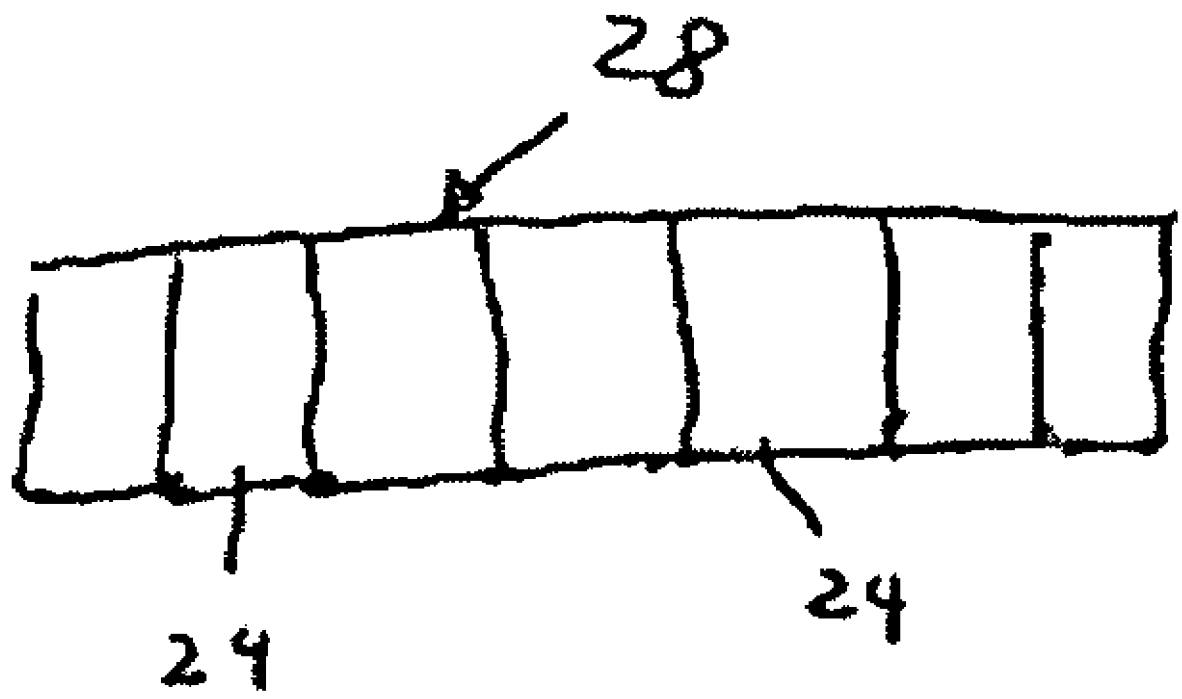
FIG. 6 illustrates an assembly of containers.

Furthermore, it is advantageous if the container 24 is provided on the outside with an image 26, in particular obtained with using a printing technique. Filter paper is eminently suitable for an image to be applied thereto, for example, with the aid of a printing technique such as a flexographic printing technique. The image 26 may in this case be applied to the filter paper before the filter paper is formed into the container 24. In this way, it is possible to provide the container 24 with an advertising message. In particular, however, it is advantageous for the container 24 in this way to be provided with an indication of the composition contained therein. Such an indication may, for example, be a brand name, but may also be a list of the ingredients or active constituents. It is also possible to provide the container 24 with warnings in this way. In order to facilitate packaging, the containers 24 may be joined together to form one or more strands 28 as illustrated in FIG. 6.

Figure 7:
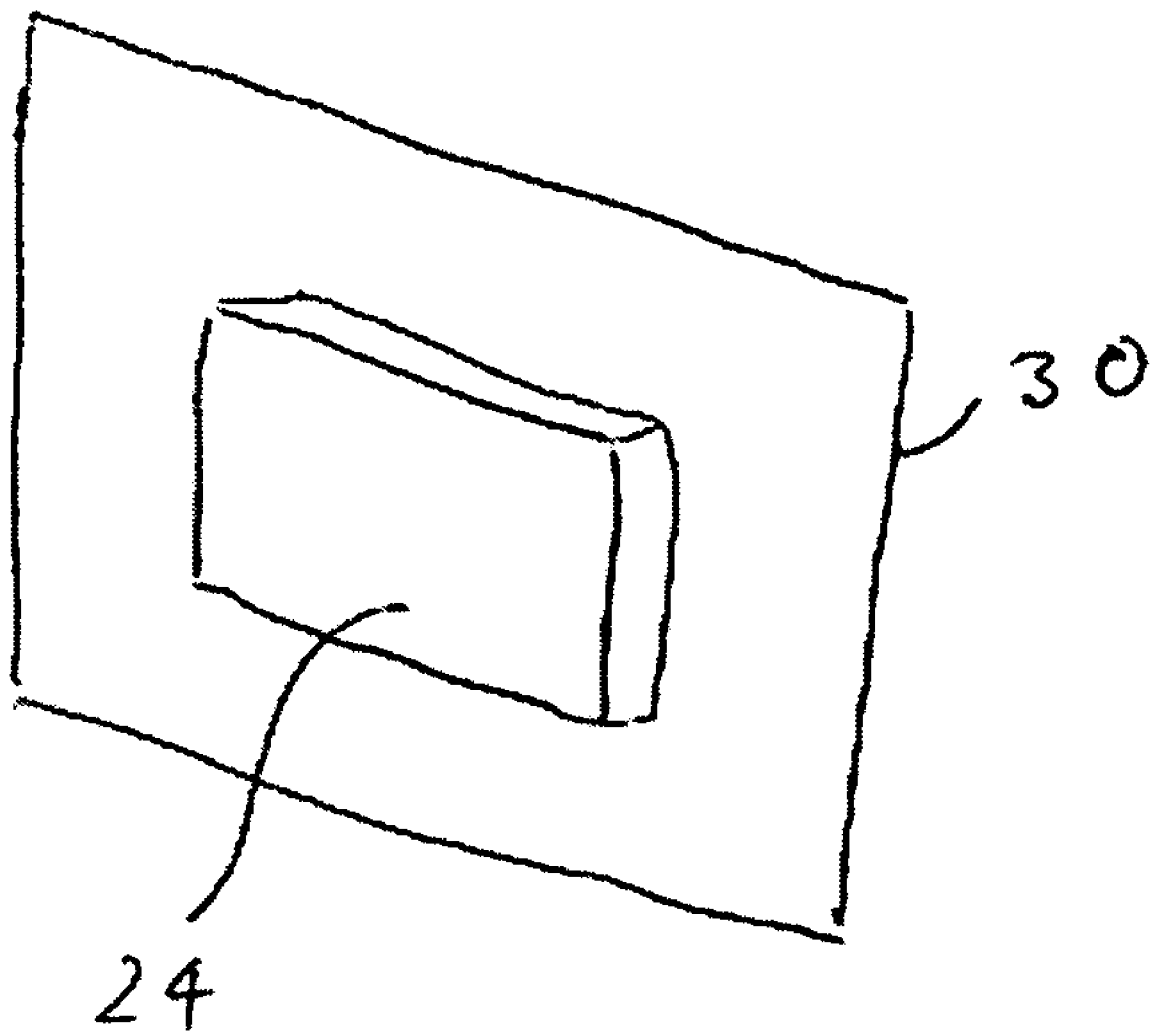
FIG. 7 illustrates a packaging assembly.

As shown in FIG. 7, the invention also provides a packaging assembly comprising a waterproof, or at least moisture-proof, outer packaging 30 containing one or more containers 24 according to the invention. A packaging assembly of this type can be used to ensure that the containers 24 arrive at the user in good condition and, moreover, can be stored in good condition for a certain time by the user. The outer packaging 30 will in this case be a waterproof or at least moisture-proof recloseable outer packaging. Consideration may be given, for example, to a plastic box or bucket with a lid which can seal onto the upper rim of the box or bucket via a, preferably clamping, labyrinth seal.

EXAMPLES (A) pH Profile of a Composition with $CaCO_3$

The present example compares the pH distribution obtained with the below example composition (1) of the invention as opposed to those yielded by (2) EZ DOSES® with no effervescing agent and (3) CHRYSAL®, two commercially available formulations. The following preparations were applied to cut flowers:

| Dextrose | Citric Acid | KAlSO$_4$ | MgSO$_4$ | Additives | NaBO$_3$.4H$_2$O | CaCO$_3$ | |
|---|---|---|---|---|---|---|---|
| 3.727 | 1.338 | 0.021 | 0.048 | 0.050 | 0.071 | 0.20 | grams |
| 3727 | 1338 | 21 | 48 | 50 | 71 | 200 | Ppm |

(1) Preparation with 4 (w/w)% CaCO$_3$, comprising the following ingredients:
(2) EZ DOSE® 5.0 g formula
(3) CHRYSAL T-BAG®

Packets for treatment (1) and (2) were made with 10 g of each formulation filled in filter paper bags. One packet was dropped into 2 L of standardized water. For treatment (3), one CHRYSAL T-BAG® packet was dropped in 1.5 L of standardized water (recommended rate). No mixing was done. An aliquot of the solution (about 30 ml) was pipetted out at different times from the top and the bottom of the solution and the pH was measured. Care was taken not to disturb the solution while pipetting.

Figure 2:
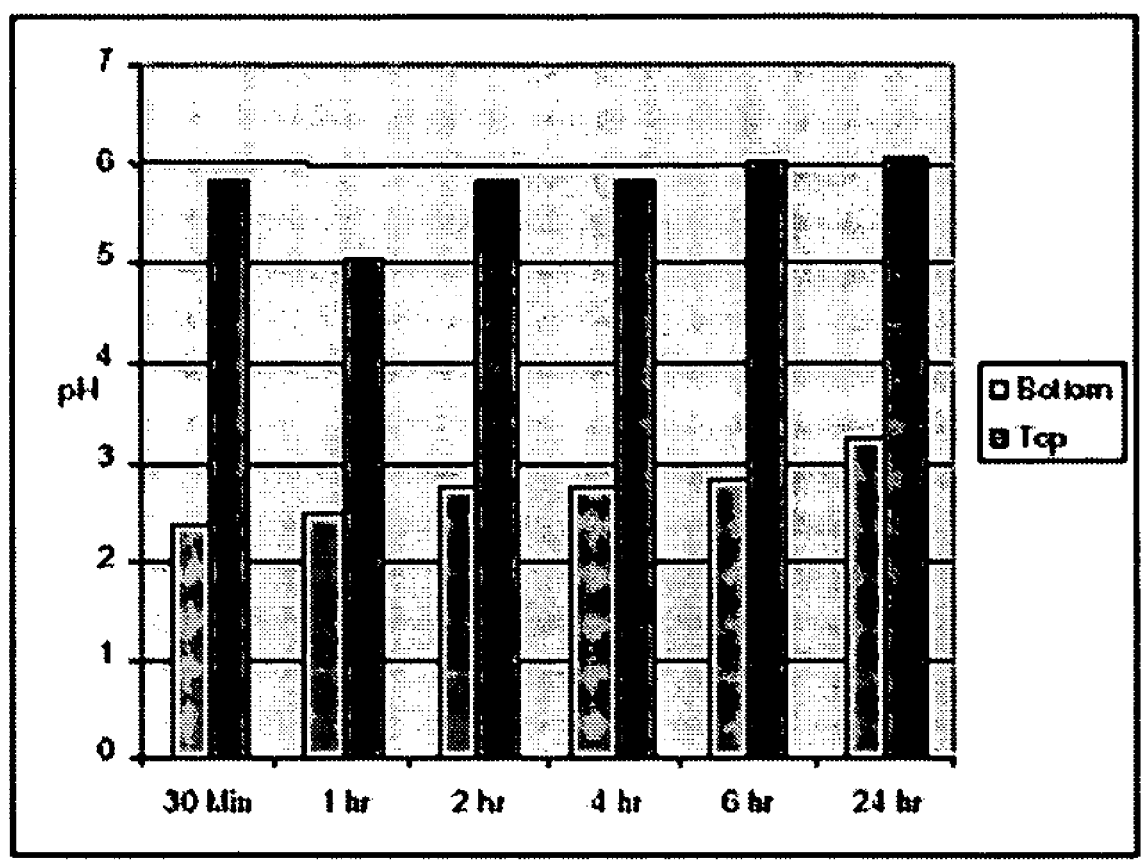
FIG. 2 illustrates the top-bottom pH differential of an unmixed aqueous solution obtained with EZ DOSE® composition without effervescing agents.
Figure 3:
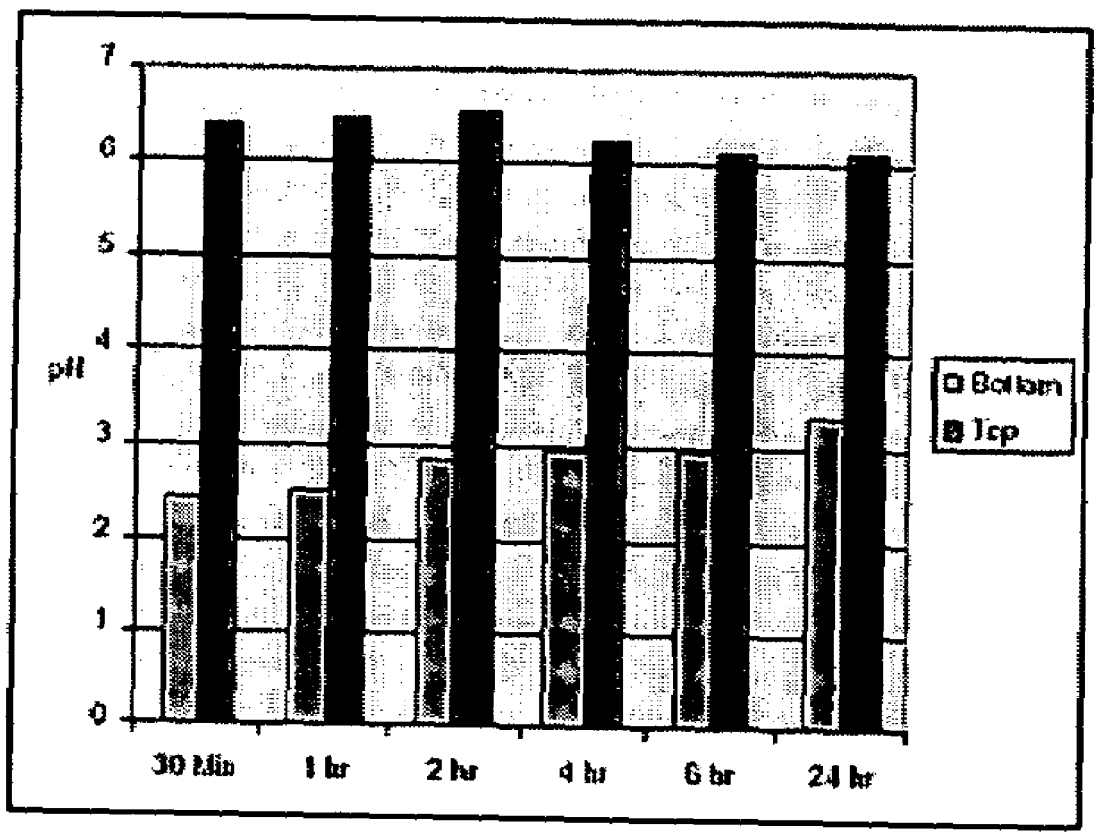
FIG. 3 illustrates the top-bottom pH differential of an unmixed aqueous solution obtained with CHRYSAL T-BAG®.

The bags with composition (1) floated to the top within 10 seconds whereas bags with compositions (2) and (3) remained at the bottom for at least 30 min. FIG. 1 illustrates the pH of the top and bottom of the solution from 30 min to 24 hr after the addition of the addition to water of the bag with composition (1). FIG. 2 illustrates the pH of the top and bottom of the solution from 30 min to 24 hr after the addition to water of the bag with composition (2). FIG. 3 illustrates the top of the top and bottom of the solution from 30 min to 24 hr after the addition to water of the bag with composition (3).

The pH of the solution after thorough mixing was 3.413, 3.324 and 3.297 for treatment (1), (2) and (3), respectively. The pH data show that the presence of CaCO$_3$ significantly improves the mixing and maintains correct pH throughout the solution within 30 min. Without CaCO$_3$, the pH does not equilibrate throughout the solution even after 24 hours.

(B) Treatment of Flowers with the Compositions of the Invention

Compositions with CaCO$_3$ were compared in their effectiveness as cut flower food to traditional formulations. All compositions were tested on Dutch rose "Abrakadabra" and Purple Lisianthus. Dutch rose crops were obtained from Blumex (Miami, Fla.). Purple Lisianthus crops were obtained from Queens, (Miami, Fla.).

Rose heads were dipped in CURALAN® (10 ml/3.785 L) fungicide to inhibit Botrytis. All stems were re-cut under clean water with MICROBLOC® (60 ml/18.93 L) disinfectant. After processing the stems were randomly placed in 1 L vases of each flower food solution, according to experimental design. pH of each solution was measured. Vase life based on overall bloom life was determined by visual observation. Days to vase cloudiness were monitored. Data were analyzed using a one-way ANOVA TM®. Each treatment was tested in three separate vases, three flowers to a vase.

The following treatments were applied to the flowers:

Treatment 1, EZ DOSE® composition without CaCO$_3$: values are grams to make up 1 L of the solution

| Dextrose | Citric Acid | KAlSO$_4$ | MgSO$_4$ | Additives | NaBO$_3$.4H$_2$O | CaCO$_3$ | |
|---|---|---|---|---|---|---|---|
| 4.272 | 0.538 | 0.021 | 0.048 | 0.050 | 0.071 | | grams |
| 4272 | 538 | 21 | 48 | 50 | 71 | | ppm |

Treatment 2, EZ DOSE® composition with 8% CaCO$_3$ and citric acid: values are grams to make up 1 L of the solution

| Dextrose | Citric Acid | KAlSO$_4$ | MgSO$_4$ | Additives | NaBO$_3$.4H$_2$O | CaCO$_3$ | |
|---|---|---|---|---|---|---|---|
| 2.248 | 2.162 | 0.021 | 0.048 | 0.050 | 0.071 | 0.40 | grams |
| 2248 | 2162 | 21 | 48 | 50 | 71 | 400 | ppm |

Treatment 3, EZ DOSE® composition with 4% CaCO$_3$ and citric acid: values are grams to make up 1 L of the solution

| Dextrose | Citric Acid | KAlSO$_4$ | MgSO$_4$ | Additives | NaBO$_3$.4H$_2$O | CaCO$_3$ | |
|---|---|---|---|---|---|---|---|
| 3.272 | 1.338 | 0.021 | 0.048 | 0.050 | 0.071 | 0.20 | grams |
| 3272 | 1338 | 21 | 48 | 50 | 71 | 200 | ppm |

Treatment 4 (HF 200 powder): values are grams to make up 1 L of the solution

| Dextrose | Citric Acid | KAlSO$_4$ | MgSO$_4$ | CaSO$_4$ | Additives |
|---|---|---|---|---|---|
| 4.40 g | 0.47 | 0.02 | 0.02 | 0.02 | 0.08 |

Treatment 5: CHRYSAL T-BAG®
Treatment 6: CHRYSAL®
Treatment 7: CHRYSAL® 2
Treatment 8: FLORALIFE CLEAR PROFESSIONAL™
Treatment 9: FLORALIFE PROFESSIONAL®
Treatment 10: standardized water EZ DOSE®, EZ DOSE® with 4% CaCO$_3$, EZ DOSE® with 8% CaCO$_3$, FLORALIFE CLEAR PROFESSIONAL™ and FLORALIFE PROFESSIONAL® increased the rose vase life compared to water. Lisianthus vase life was increased by all the treatments compared to water. Flowers treated in solutions of EZ DOSE® with 4% CaCO$_3$ and of EZ DOSE® with 8% CaCO$_3$ also exhibited a more complete, homogeneous opening. The foliage of such flowers also maintained a healthy and well-hydrated appearance.

TABLE 1

Vase life of flowers and days to vase cloudiness

| Treatment | Rose vase life | Lisianthus vase life | Days to vase cloudiness |
|---|---|---|---|
| EZ DOSE ® | 10.5 | 9.1 | 10.3 |
| EZ DOSE ® with 8% CaCO$_3$ | 9.6 | 9.2 | 13.3 |
| EZ DOSE ® with 4% CaCO$_3$ | 9.8 | 10.1 | 11.3 |
| Powder HF200 ™ | 9.2 | 9.2 | 6.7 |
| CHRYSAL T-BAG ® | 9.1 | 8.7 | 6.7 |
| RIPPIT ® | 9.3 | 8.0 | 6.3 |
| CHRYSAL ® 2 | 9.3 | 9.6 | 8.0 |
| FLORALIFE CLEAR PROFESSIONAL ™ | 10.0 | 9.1 | 7.7 |
| FLORALIFE PROFESSIONAL ® | 10.4 | 9.7 | 8.3 |
| Standardized water | 7.4 | 4.3 | 7.7 |

As set forth in Table 1, the performance of EZ DOSE® with CaCO$_3$ in terms of flower vase life is comparable to that obtained by EZ DOSE® without CaCO$_3$. Addition of CaCO$_3$ up to 8% has therefore no significant negative effect on the vase life performance of the formulation.

As is apparent from the foregoing specification, the invention is susceptible of being embodied with various alterations and modifications which may differ particularly from those that have been described in the preceding specification. It should be understood that the inventor wishes to embody within the scope of the patent warranted hereon all such modifications as reasonably and properly come within the scope of his contribution to the art.

The invention claimed is:

1. In a kit comprising a composition for cut flowers and a permeable or semi-permeable container, the improvement comprising the composition comprising components that yield gaseous decomposition products in an amount sufficient to cause the container to float after the container is placed into a vessel with water therein.

2. A cut flower food packet comprising:
an at least semi-permeable container having a permeability to particles of a size no greater than 400 μm, and a composition for cut flowers in the container comprising one or more compounds that produce gas when contacted with water in an amount sufficient to cause the container to float after the container is placed into a vessel with water therein.

3. The packet of claim 2, wherein said compounds are selected from the group consisting of carbonates and bicarbonates.

4. The packet of claim 3, wherein the carbonates and bicarbonates are selected from the group consisting of Li$_2$CO$_3$, Na$_2$CO$_3$, K$_2$CO$_3$, (NH$_4$)$_2$CO$_3$, MgCO$_3$, CaCO$_3$ LiHCO$_3$, NaHCO$_3$ KHCO$_3$ and NH$_4$HCO$_3$.

5. The packet of claim 3 wherein the carbonate is CaCO$_3$.

6. The packet of claim 5, wherein a ratio of a weight of the CaCO$_3$ to a total weight of the composition is 0.5 :100 to 10 :100.

7. The packet of claim 5, wherein said ratio is 2:100 to 5 :100.

8. The packet of claim 5, wherein said ratio is 2.8 :100 to 4:100.

9. The packet of claim 2, wherein said container has a permeability to particles of a size no greater than 100 μm.

10. The packet of claim 2, further comprising at least one or more acids.

11. The packet of claim 10, wherein said acids are selected from the group consisting of formic, acetic, propionic, butanoic, pentanoic, hexanoic, malonic, tartaric, ascorbic and citric.

12. The packet of claim 11, wherein the acid is citric acid.

13. The packet of claim 2, further comprising one or more carbohydrates.

14. The packet of claim 13, wherein the carbohydrate is dextrose.

15. The packet of claim 2, further comprising one or more sulfates.

16. The packet of claim 15, wherein the sulfates are selected from the group consisting of KAl(SO$_4$)$_2$ and MgSO$_4$.

17. The packet of claim 2, further comprising one or more additives selected from the group consisting of disinfectants, biocides and growth regulators.

18. The packet of claim 17, wherein said growth regulators are selected from the group consisting of auxins, cytokinins and gibberellins.

19. The packet of claim 2, further comprising sodium perborate.

20. The packet of claim 2, further comprising one or more drying agents.

21. The packet of claim 2, wherein the container is rectangular in shape with dimensions of 2 cm to 8 cm wide by 2 to 12 cm long.

22. The packet of claim 2, wherein the container comprises an image.

23. The packet of claim 22, wherein the image is obtained using a printing technique.

24. The packet of claim 22, wherein the image comprises instructions for use or application.

25. An assembly of containers according to claim 2, wherein the containers are joined together to form one or more strands.

26. An assembly comprising a waterproof or moisture-proof outer packaging and one or more packets according to claim 2.

27. A method for maintaining the freshness of cut flowers comprising:
placing stems of cut flowers in a vase,
placing water in the vase, placing a cut flower food packet in the vase which comprises an at least semi-permeable container having a permeability to particles of a size no greater than 400 µm, and a composition for cut flowers in the container comprising one or more compounds that produce gas when contacted with water in an amount sufficient to cause the container to float afier the container is placed into the vase with water therein, and then allowing the container to float to the surface of the water in the vase.

28. A method according to claim 27, wherein said compounds form an aqueous solution comprising 0.05 g/L to 0.8 g/L of $CaCO_3$ and 0.2 g/L to 3 g/L of citric acid.

29. A method according to claim 27, wherein said compounds form an aqueous solution comprising 0.2 g/L to 0.4 g/L of $CaCO_3$ and 0.5 g/L to 2.5 g/L of citric acid.

30. A method according to claim 27, wherein said compounds form an aqueous solution comprising 1 g/L to 6 g/L of dextrose, 0.005 g/L to 0.04 g/L of KA 1 $(SO_4)_2$ and 0.02 g/L to 0.08 g/L of $MgSO_4$.

31. A method according to claim 27, wherein said compounds form an aqueous solution comprising 2 g/L to 4.5 g/L of dextrose, 0.01 g/L to 0.03 g/L of $KA1(SO_4)_2$ and 0.03 g/L to 0.07 g/L of $MgSO_4$.

32. A cut flower maintained fresh according to the method of claim 28.

33. A cut flower maintained fresh according to the method of claim 29.

34. A cut flower maintained fresh according to the method of claim 30.

35. A cut flower maintained fresh according to the method of claim 31.

36. The packet of claim 2, wherein the composition comprises one more compounds selected from the group consisting of compounds comprising one or more azo-moieties, compounds comprising one or more diazo- moieties, chlathrates, $Li_2O_2$, $Na_2O_2$, $K_{2\,O2}$ and $MgO_2$, borax and $NaBO_3$.

37. A cut flower food packet comprising:
an at least semi-permeable container having a permeability to particles of a size no greater than 400 µm, and
a composition for cut flowers in the container wherein 100 g of said composition comprise:
2 g to 10 of $CaCO_3$, and
10 g to 60 g of citric acid said composition being provided in said container in an amount sufficient to cause the container to float due to a release of gas from said composition afier the container is placed into a vessel with water therein.

38. The packet of claim 37, wherein 100 g of said composition comprise:
4 g to 8 g of $CaCO_3$, and
20 g to 40 g of citric acid.

39. The packet of claim 37, wherein 100 g of said composition further comprise:
20 g to 95 g of one or more carbohydrates,
0.2 g to 0.6 g of $KAl(SO_4)_2$ and 0.6 gto 1.4 g of $MgSO_4$.

40. A cut flower food packet comprising:
an at least semi-permeable container having a permeability to particles of a size no greater than 400 µm, and
a composition for cut flowers in the container comprising components that yield gaseous decomposition products in an amount sufficient to cause the container to float after the container is placed into a vessel with water therein.

\* \* \* \* \*